United States Patent [19]

Louderback

[11] 4,360,275
[45] Nov. 23, 1982

[54] DEVICE FOR MEASUREMENT OF OPTICAL SCATTERING

[75] Inventor: Anthony W. Louderback, Ojai, Calif.

[73] Assignee: Litton Systems Inc., Beverly Hills, Calif.

[21] Appl. No.: 176,880

[22] Filed: Aug. 11, 1980

[51] Int. Cl.³ .......................... G01N 21/47; G02B 5/10
[52] U.S. Cl. ........................................ 356/446; 350/296
[58] Field of Search ............................... 356/338–342, 356/445–448; 372/99; 350/296

[56] References Cited

U.S. PATENT DOCUMENTS

| | | | |
|---|---|---|---|
| 3,504,983 | 4/1970 | Richmond et al. | 356/445 |
| 4,188,543 | 2/1980 | Brunsting et al. | 356/339 |

FOREIGN PATENT DOCUMENTS 55-70732   5/1980   Japan .................................. 356/338

OTHER PUBLICATIONS

Smith, I. W., "Reflectometer for Laser Mirrors with Accuracy Better than 10⁻⁴", Applied Optics, vol. 17, No. 16, Aug. 15, 1978, pp. 2476–2477.

*Primary Examiner*—Bruce Y. Arnold

[57] ABSTRACT

There is disclosed a device for measuring total diffuse optical scattering from the surface of a sample, including a surface having extremely low scatter. A light beam from a laser is directed through an entrance hole in an ellipsoidal reflector and through the vicinity of a first focus of the reflector. The reflector has a first aperture adjacent the first focus for receiving a sample to be measured and a second aperture adjacent a second focus for receiving a photoresponsive means. A sample mounting means is used to position the sample at the first focus and to orient the sample so that the portion of the light beam which is specularly reflected from the sample is directed out of an exit hole located in the reflector diametrically opposite to the entrance hole. A major portion of the light diffusely scattered from the sample into a $2\pi$ solid angle (hemisphere) reaches the second aperture either directly or by a single reflection from the reflector. The photoresponsive means such as a photomultiplier is positioned at the second aperture for detecting the magnitude of light scattered.

In a specific embodiment, the ellipsoidal reflector is easily and cheaply made from two half-ellipsoidal mirrors which are joined together at their wide ends.

9 Claims, 1 Drawing Figure

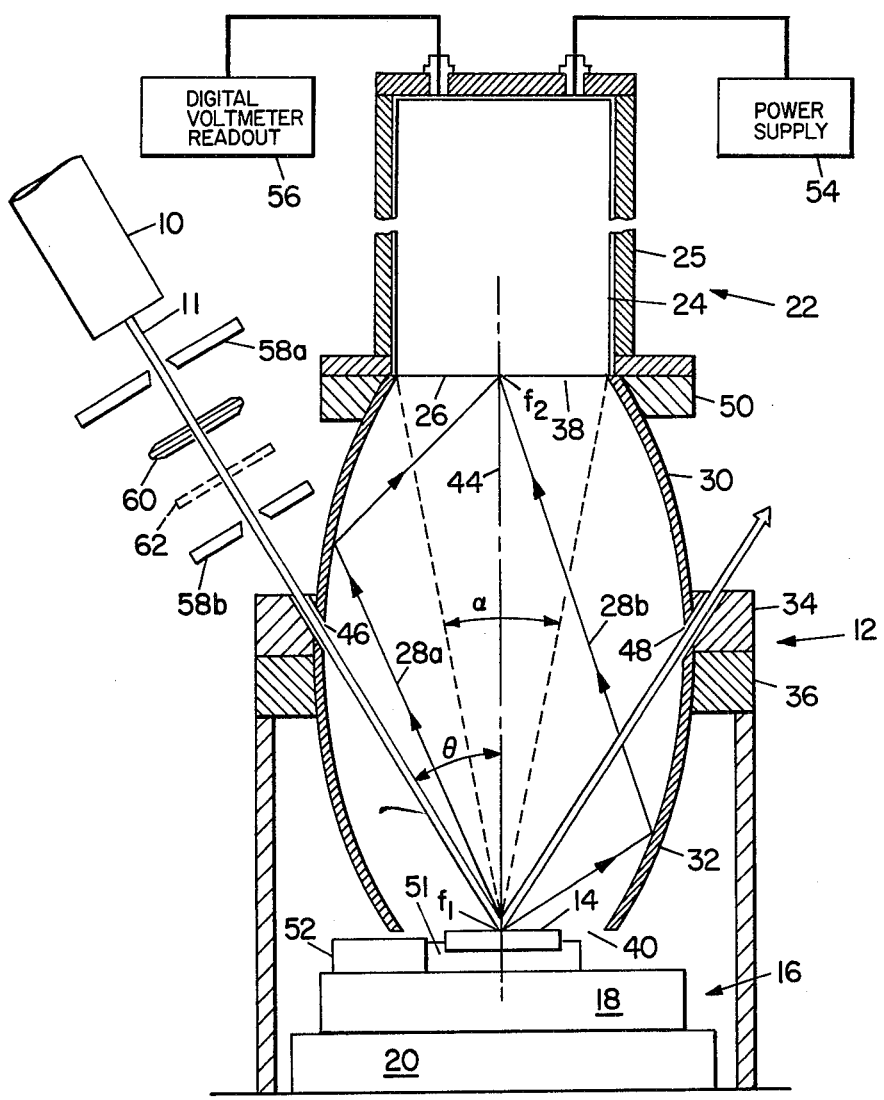

DEVICE FOR MEASUREMENT OF OPTICAL SCATTERING

TECHNICAL FIELD

The present invention relates in general to optical measurement devices and in particular to optical devices for measuring the amount of light scattered from a surface.

BACKGROUND ART

For certain types of reflective optical systems it is important that the component reflecting surfaces have low total optical scatter. For the purposes of this application, the total optical scatter is defined as the ratio of the energy diffusely scattered by a reflecting surface into a $2\pi$ solid angle (a hemisphere) from a beam of light incident on the surface to the energy of the incident beam.

One type of system requiring such low scatter mirrors is the ring laser gyro. In a ring laser gyro two laser beams are generated in opposite directions of propagation about a closed loop path formed by three or more mirrors. The path encloses the axis of rotation about which an angular rotation rate is to be sensed. Rotation of the apparatus about this axis causes a frequency difference between the two beams which provides a readout of rotation rate. However, difficulty arises at low rotational rates because the scattering of the beams from the mirrors causes the two beams to tend to oscillate at only one frequency or to "lock-in." Lock-in makes it impossible to measure rotational rates because the frequency difference disappears even though the rotation rate of the gyro is not zero.

As is well known the lower the mirror scattering, the lower is the lock-in frequency and hence the lower the minimum measurable rotation rate. Ring laser gyros therefore require mirrors having extremely low scattering in order to adequately measure low rotation rates. As an example, a satisfactory mirror must typically scatter no more than a few parts in ten thousand of the incident laser beam. Fabrication of such mirrors requires the deposition on a mirror substrate of a reflective coating comprising a stack of dielectric layers specifically designed for low scatter. Such a reflective coating is described, for example, in U.S. Pat. No. 4,142,958 issued to D. Wei and A. Louderback on Mar. 6, 1979 and assigned to the assignee of the present invention.

Efficient fabrication of these mirrors requires a device called a scatterometer for measuring the amount of light each mirror scatters prior to its installation in a laser gyro. A problem which arises is that conventional scatterometers lack the capability to easily and accurately measure the low levels of light involved. In one such conventional instrument, an integrating sphere scatterometer, the light scattered from the mirror sample being measured is directed into the interior of a sphere having a coating which diffusely scatters light falling upon it. Thus scattered, the light uniformly illuminates the interior of the sphere. A photosenser views the interior surface through a small window in the wall of the sphere and thereby produces an output signal proportional to the total scattering of the mirror. One of the drawbacks of the integrating sphere scatterometer is the low measurement sensitivity resulting from the fact that only a small fraction of the total light scattered is intercepted by the photosensor. Hence, low level scattering is difficult to measure.

Another type of prior art scatterometer measures scattering over a range of small solid angles. By adding up the scattering from each increment of solid angle, a total scatter is obtained. However, equipment to accomplish this is expensive and the measurement process is laborious.

SUMMARY OF THE INVENTION

Accordingly, it is an object of the present invention to provide an inexpensive device for measuring the total amount of light scattered from a surface quickly, easily, and reliably.

A further object is to provide such a device which can measure very low levels of scattered light with a high degree of accuracy.

These and other objects and advantages are accomplished in a scatterometer in which a light beam from a light source such as a laser is directed through an entrance hole in an ellipsoidal reflector and through the vicinity of a first focus of the reflector. The reflector has a first aperture adjacent the first focus for receiving a sample to be measured and a second aperture adjacent a second focus for receiving a photoresponsive means. A sample mounting means is used to position the sample at the first focus and to orient the sample so that the portion of the light beam which is specularly reflected from the sample is directed out of an exit hole located in the reflector diametrically opposite to the entrance hole. A major portion of the light diffusely scattered by the sample into a $2\pi$ solid angle reaches the second aperture either directly or by a single reflection from the reflector. The photoresponsive means such as a photomultiplier is positioned at the second aperture for detecting the scattered light.

In a specific embodiment, the ellipsoidal reflector is easily and cheaply made from two half ellipsoidal mirrors which are readily procured commercially at low cost and then joined together at their wide ends.

BRIEF DESCRIPTION OF DRAWING

These and other objects, advantages, and features will become more fully apparent from the following detailed description of the invention when considered in conjunction with the accompanying FIGURE which is a diagrammatic view of the embodiment of the scatterometer of the present invention.

DETAILED DESCRIPTION OF THE PREFERRED EMBODIMENT

Referring with particularity to the drawing, the construction of the invention is illustrated. The main components of the scatterometer include a light source means such as a laser 10 for generating a light beam 11, an ellipsoidal reflector 12 having a lower or first focus $f_1$ and an upper or second focus $f_2$ for collecting light scattered by a sample 14 being measured, and a sample mounting means 16. The scatterometer further includes a photoresponsive means 22, preferably comprising a photomultiplier tube 24 having a photosensitive surface 26 which detects the scattered light leaving sample 14. Photomultiplier tube 24 is mounted in photomultiplier housing 25.

The ellipsoidal reflector 12 has the known property that all liight rays leaving either focus will, upon one reflection from the reflecting surface, pass through the other focus, as illustrated by scattered light rays 28a and 28b. The reflector 12 is constructed from two identical upper and lower half-ellipsoidal mirrors 30 and 32, respectively, which are joined together at their wide ends by upper and lower flanges 34 and 36. The reflectors 30 and 32 are made of metal with the interior, reflective surfaces coated with rhodium having an approximate average reflectance of 80% in the visible wavelength region. The reflectors are commercially available at low cost from Melles Griot, Inc., Irvine, Calif. as part number 02REM001.

Using conventional machining techniques, top and bottom apertures 38 and 40 are respectively cut out of reflectors 30 and 32 at their closed ends, that is the end adjacent to each focus. The plane of each of these apertures is substantially perpendicular to the common axis 44 joining foci $f_1$ and $f_2$ and intersects axis 44 at approximately either focus of reflector 12. Ellipsoidal reflector 12 also includes an entrance hole 46 and a diametrically opposed exit hole 48 for permitting light beam 11 from laser light source 10 to enter and exit the reflector 12. The holes are drilled at an angle to common axis 44 at which it is desired to illuminate sample 14. In the embodiment shown, beam 11 impinges sample 14 at an angle of incidence to the normal to sample 14 of $\theta = 45$ degrees. At this angle, the holes 46 and 48 are located in upper reflector 30 just inside its lip, as shown.

Of course mirror 12 could have been made from a single ellipsoidal mirror rather than the two half-ellipsoidal mirrors 30 and 32, but its cost would rise by many times and its fabrication become highly complex. Therefore the two-piece mirror construction described here is a key factor in keeping down the overall cost and enhancing the ease of construction of the invention.

Photomultiplier housing 25 is fastened to the top of reflector 12 by means of flange 50.

Mounting flanges 34, 36 and 50 are separately fabricated and then bonded to the outer surface of reflector 12 by conventional adhesive material.

The laser light source 10 operates at a predetermined wavelength at which it is desired to measure scattering from sample 14. In the present embodiment, the lasing medium is a mixture of helium and neon gas producing an output wavelength of 6328 A. The laser 10 is positioned to direct the output beam 11 through reflector entrance hole 46 so as to pass through the vicinity of focus $f_1$.

The sample mounting means 16 includes a two-axis tilt table 18 and a three-axis translation table 20 which are used to position the sample 14. Suitable tilt and translation tables are available from Newport Research Corp., Fountain Valley, Calif., as Model 405 Dual Axis Translation Table, and Model 39 Tilt Platform, respectively. Prior to mounting sample 14 to sample mounting means 16, sample 14 is inserted into a holder 51 and then positioned on the top surface of tilt table 18 against positioning rail 52. Thus mounted to sample mounting means 16, sample 14 is moved vertically by translation table 20 to position its upper surface at the first focus $f_1$, the point where laser beam 11 impinges.

After reflection from sample 14, the laser beam 11 is directed out through exit hole 48 by properly orienting sample 14 with tilt table 18.

The light scattered from the illuminated spot on sample 14 can be divided into two angular portions, a portion within angle $\alpha$ and the remaining portion outside of angle $\alpha$, where angle $\alpha$ is the angle subtended at the illuminated sample spot by the top aperture 38. In practice, angle $\alpha$ is determined by the geometry of reflector 12 which in turn, governs the size of aperture 38. The diameter of photosensitive surface 26 is selected to be approximately equal to the diameter of aperture 38 so that at least most of the light scattered within angle $\alpha$ is received directly by photosensitive surface 26. The portion of light outside of angle $\alpha$, as represented by rays 28a and 28b, after a single reflection from the reflecting surface of ellipsoidal mirror 12, is directed to upper focus $f_2$ and thereby also collected by photosensitive surface 26.

One advantage of completely filling upper aperture 38 with photosensitive surface 26 is that all scattered light from sample 14, no matter how poorly focussed in the region of focus $f_2$, will still be collected by the photosensitive surface. Therefore large imperfections in the surface figure of reflector 12 and inaccurate placement of the illuminated spot with respect to focus $f_1$ will not significantly lower the measurement accuracy.

Prior to entering entrance hole 46, laser beam 11 passes through a series of baffles 58a and 58b. Each of the baffles 58a and 58b comprise a metal plate having an aperture slightly larger than the light beam 11. The baffles are positioned between the laser light source 10 and entrance hole 46 with the aperture centered about the beam. These baffles block nonparallel light such as is created by surface reflections from the laser output mirror as well as by laser discharge light. If not blocked, a portion of this nonparallel light could enter through entrance hole 46, and after one or more reflections from sample 14 and the reflector 12, be collected by photomultiplier 24 to thereby overwhelm the much weaker scattered light.

The sizes of entrance hole 46 and exit hole 48 are just slightly larger than the beam 11 so as not to intercept any of the specular component of the beam leaving sample 14, but are small enough to avoid losing as little as possible of the light scattered from sample 14. These requirements are easily met in the specific embodiment of the invention in which beam 11 is a laser beam 0.080 inch in diameter and entrance and exit holes 46 and 48 are each 0.125 inch in diameter. With the ellipsoidal mirror 12 having a minor axis of approximately 3 inches and a total surface area of approximately 40 square inches, a total of less than one percent of scattered light is lost through both entrance and exit holes 46 and 48.

If it is desired to illuminate a spot on sample 14 that has a smaller dimension than the beam diameter exiting source 11, lens 60 can be inserted in front of the laser to thereby focus the beam to form a reduced spot size on sample 14.

Photomultiplier 24 is energized by a power supply 54. As is well known, the photomultiplier produces a signal proportional to the light energy incident upon its photosensitive surface 24. The signal output is read by an output indicator such as a digital voltmeter 56.

Prior to measurement of scattering, the instrument must first be calibrated by measuring its output for a known amount of light scattering. This is accomplished by inserting in place of sample 14 a scattering sample having a known amount of scattering, such as a disk covered with barium sulfate ($BaSO_4$) having a 99% diffuse scattering. In addition, an optical filter 62 having a known, low transmittance is inserted within beam 11 in between the output of laser source 10 and the entrance hole 46. The purpose of optical filter 62 is to avoid exposing the sensitive photomultiplier tube to a high level of light that would saturate or even damage it. Preferably, filter 62 comprises a transparent substrate coated with a metal film having a transmission of 0.1%. With the beam 11 incident on the calibration sample, the voltage of the photomultiplier tube 24 is adjusted by adjusting power supply 54 so that the voltmeter readout 56 reads the known transmittance of the optical filter 62 directly.

To perform a scattering measurement on the mirror sample 14, the sample 14 is inserted into its mirror holder 51 and positioned on the top surface of tilt table 18 against positioning rail 52. The sample is then raised by adjusting translation table 20 until the top surface of sample 14 is at the same height as the reflector aperture 40. The sample alignment is accomplished by adjusting translation table 20 in height and tilt table 18 in angle until the laser beam 11 reflected from sample 14 is seen to leave exit hole 48. The photomultiplier power supply 54 is then turned on and further adjustment of translation table 20 and tilt table 18 are carried out to minimize the voltmeter readout 56. When a minimum voltmeter reading is reached by sequential adjustments of height and tilt, the light beam 11 is then centered in exit hole 48. At this position, small changes in sample height or tilt will not change the voltmeter reading. The scattering value is then read directly on the voltmeter readout. Scattering from various spots on sample 14 can be measured by simply moving the position of the sample 14 by using the horizontal controls of the translation table.

During both measurement and calibration operations, room lights must be extinguished so as to not influence the photomultiplier readings. In order that the photomultiplier tube 24 not be damaged if the laser beam is inadvertently reflected directly onto it, the photomultiplier tube must be turned off during the initial sample alignment.

If the laser light source 10 is selected to have a linearly polarized output beam, then the scattering of light beam 11 having either s-polarization or p-polarization light can be measured. The polarization vector is perpendicular to the plane of incidence for s-polarization and parallel to the plane of incidence for s-polarization. The polarization is changed simply by rotating the laser head in its mount. In general, this may require realignment of the beam direction and the sample 14 so that the light beam 11 remains centered in entrance and exit holes 46 and 48.

As an illustrative example of the performance of the above described invention, the instrument was used to measure total scattering from mirror samples having total scatter of as low as 15 parts per million. Repeatability of scattering values was better then one part per million, with an absolute accuracy of better than plus or minus 20%.

While the scatterometer of the present invention has been described in detail above, and a presently preferred embodiment has also been described, it will be appreciated that there may be modifications to the embodiment and therefore the scope of the invention is not to be limited except by the following claims. For example, since the device is basically all reflecting, any optical wavelength in which the photoresponsive means 22 is sensitive may be used. Therefore scattering may be measured at differing wavelengths by simply substituting light sources of different output wavelengths. In addition the angle of incidence of beam 11 may be varied by locating the entrance and exit holes 46 and 48 at other positions in the reflector. Moreover, the scattering for normal incidence of illumination can be measured by simply orienting sample 14 perpendicularly to the incoming beam 11 so that the reflected beam goes back out through entrance hole 46.

What is claimed is:
1. A device for measuring light scattered from a sample surface comprising:
   (a) a substantially ellipsoidal reflector having a first aperture adjacent a first focus of said substantially ellipsoidal reflector for receiving a sample to be measured and a second aperture adjacent a second focus of said ellipsoidal reflector, said substantially ellipsoidal reflector additionally having an entrance hole and an exit hole through which a light beam respectively enters and exits said ellipsoidal reflector;
   (b) light source means for producing a collimated light beam directed along a path passing through said entrance hole of said substantially ellipsoidal reflector and through the vicinity of said first focus of said substantially ellipsoidal reflector;
   (c) mounting means for positioning said sample surface substantially at said first focus and for orienting said surface so that the portion of said light beam which is specularly reflected from said sample is directed out of said exit hole; and,
   (d) photoresponsive means positioned at said second aperture for detecting at least most of the light scattered from said incident light beam by said sample surface which reaches said second aperture.

2. The device of claim 1 wherein said photoresponsive means includes a photodetector having its photosensitive surface positioned at said second focus and filling said second aperture.

3. The device of claim 2 wherein said photoresponsive means includes a photomultiplier.

4. The device of claim 1 wherein said light source means includes a laser.

5. The device of claim 4 wherein said laser operates with a mixture of helium and neon gases and has an optical output wavelength of substantially 6328 A.

6. The device of claim 1 further comprising one or more baffle plates, each plate containing a round aperture slightly larger than the laser beam, said plate positioned between said light source and said entrance hole of said reflector so that said light beam passes through the center of said aperture.

7. The device of claim 1 wherein said beam has an angle of incidence to said sample of substantially 45 degrees.

8. The device of claim 1 wherein said reflector comprises two-half ellipsoidal reflectors having their wide ends in abutting relationship.

9. The device of claim 1 further comprising a lens positioned within said light beam to bring said beam to a focus at said sample whereby said beam illuminates a reduced area of said mirror.

* * * * *